United States Patent
Manwaring et al.

(10) Patent No.: US 10,682,258 B2
(45) Date of Patent: *Jun. 16, 2020

(54) EPITHELIALIZATION METHODS, DRESSINGS, AND SYSTEMS

(71) Applicant: KCI Licensing, Inc., San Antonio, TX (US)

(72) Inventors: Michael Manwaring, San Antonio, TX (US); Robert Peyton Wilkes, San Antonio, TX (US); Braden King-Fung Leung, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 1142 days.

This patent is subject to a terminal disclaimer.

(21) Appl. No.: 14/325,505

(22) Filed: Jul. 8, 2014

(65) Prior Publication Data

US 2014/0323940 A1 Oct. 30, 2014

Related U.S. Application Data

(63) Continuation of application No. 13/045,663, filed on Mar. 11, 2011, now Pat. No. 8,808,258.

(Continued)

(51) Int. Cl.
*A61F 13/00* (2006.01)
*A61M 1/00* (2006.01)
*A61K 9/70* (2006.01)

(52) U.S. Cl.
CPC .. *A61F 13/00021* (2013.01); *A61F 13/00063* (2013.01); *A61M 1/0088* (2013.01);
(Continued)

(58) Field of Classification Search
CPC ............. A61M 1/0088; A61M 2210/04; A61F 13/00068; A61F 2013/000089; A61F 13/00063; A61F 13/00021

See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Tatyana Zalukaeva
*Assistant Examiner* — Sara A Sass

(57) ABSTRACT

Methods, dressings, and systems for promoting epithelialization of a wound or other tissue are presented. The methods, dressings, and systems help form simulated rete pegs. In one instance, an epithelialization dressing is disclosed that may include a dressing body having a plurality of projections. A plurality of apertures is formed on a portion of the dressing body. The dressing helps manage fluids on the wound and the projections form cavities into which epithelial tissue migrates to from epithelial columns that function like rete pegs. Other dressings, methods, and systems are disclosed.

5 Claims, 6 Drawing Sheets

Related U.S. Application Data

(60) Provisional application No. 61/314,274, filed on Mar. 16, 2010, provisional application No. 61/314,236, filed on Mar. 16, 2010.

(52) U.S. Cl.
CPC .......... A61F 13/00068 (2013.01); A61F 2013/00089 (2013.01); A61M 2210/04 (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A * | 8/1996 | Gross ............ A61M 1/0088 604/313 |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,808,258 B2 * | 8/2014 | Manwaring ...... A61M 1/0088 602/55 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0079852 A1 | 4/2006 | Bubb et al. | |
| 2008/0177253 A1 | 7/2008 | Boehringer et al. | |
| 2008/0275409 A1 * | 11/2008 | Kane ............... A61F 13/0203 604/305 |
| 2009/0221977 A1 * | 9/2009 | Blott ............... A61M 1/0058 604/290 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| JP | 2006-149818 A | 6/2006 |
| JP | 2007-130417 A | 5/2007 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 9522305 A1 | 8/1995 |

(56) References Cited

FOREIGN PATENT DOCUMENTS

| WO | 96/05873 | 2/1996 |
|---|---|---|
| WO | 97/18007 | 5/1997 |
| WO | 99/13793 | 3/1999 |
| WO | 0185248 A1 | 11/2001 |
| WO | 2008104609 A1 | 9/2008 |
| WO | 2008141228 A1 | 11/2008 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
Canadian Examiner's Report for corresponding Application No. 2790419, dated Nov. 25, 2016.

* cited by examiner

EPITHELIALIZATION METHODS, DRESSINGS, AND SYSTEMS

RELATED APPLICATION

This application is a continuation of U.S. patent application Ser. No. 13/045,663, entitled "Epithelialization Methods, Dressings, and Systems," filed 11 Mar. 2011 which claims the benefit, under 35 USC § 119(e), of the filing of U.S. Provisional Patent Application Ser. No. 61/314,274, entitled "Patterned Neo-Epithelialization Dressings, Systems, and Methods," filed 16 Mar. 2010, and U.S. Provisional Patent Application Ser. No. 61/314,236, entitled "Epithelialization Methods, Dressings, and Systems," filed 16 Mar. 2010, each of which is incorporated herein by reference for all purposes.

BACKGROUND

The disclosure herein relates generally to medical wound care systems, and more particularly, to epithelialization methods, dressings, and systems using reduced pressure.

Depending on the medical circumstances, reduced pressure has been used for, among other things, reduced-pressure therapy to encourage granulation at a tissue site. In the normal healing process of a wound, epithelialization (or re-epithelialization since epithelium is actually growing to replace lost epithelium) takes place after granulation and can present a number of issues.

SUMMARY

According to an illustrative, non-limiting embodiment, a method for treating a wound having granulation tissue in a wound bed includes the steps of deploying an epithelialization dressing proximate the granulation tissue in the wound bed, causing a compression force on the epithelialization dressing such that a plurality of projections impinge upon the granulation tissue, and allowing sufficient time for epithelium tissue to form proximate the projections. The epithelialization dressing includes a dressing body and the plurality of projections. Each projection has a proximal end and a distal end, and the proximal end is coupled to a second, tissue-facing side of the dressing body.

According to another illustrative, non-limiting embodiment, a method for promoting healing of a wound having a wound bed includes the steps of forming granulation tissue in the wound bed with a system to promote granulation, creating a plurality of cavities in the granulation tissue with an epithelialization dressing, and creating a plurality of epithelial columns as epithelial tissue migrates into the cavities. The epithelialization dressing includes a plurality of projections that create the plurality of cavities in the granulation tissue.

According to another illustrative, non-limiting embodiment, a method of forming simulated rete pegs in a wound between granulation tissue and epithelium includes providing a plurality of projections, placing the plurality of projections proximate to the granulation tissue, causing the plurality of projections to impinge upon the granulation tissue, and allowing sufficient time for epithelial migration around the plurality of projections whereby simulated rete pegs are formed. The simulated rete pegs help anchor adjacent tissue layers.

According to another illustrative, non-limiting embodiment, an epithelialization dressing for forming anchor points between two adjacent tissue layers includes a dressing body and a plurality of projections. The dressing body has a first side and a second, tissue-facing side. Each projection has a proximal end and a distal end, and each proximal end is coupled to the second, tissue-facing side of the dressing body. The epithelialization dressing further includes a first plurality of apertures formed on a portion of the dressing body and sub-features formed on the distal end of each of the plurality of projections.

According to another illustrative, non-limiting embodiment, a system for promoting epithelialization of a wound includes an epithelialization dressing, a sealing member for forming a fluid seal over the wound and epithelialization dressing, a reduced-pressure interface for providing reduced pressure to the epithelialization dressing, and a reduced-pressure source fluidly coupled to the reduced-pressure interface. The epithelialization dressing includes a dressing body and a plurality of projections. The dressing body has a first side and a second, tissue-facing side. Each projection has a proximal end and a distal end. Each proximal end is coupled to the second, tissue-facing side of the dressing body. The dressing body also has a plurality of apertures formed on a portion of the dressing body and sub-features formed on the distal end of each of the plurality of projections.

According to another illustrative, non-limiting embodiment, a method of manufacturing an epithelialization dressing includes forming a dressing body, having a first side and a second side, from a medical-grade polymer, and forming a plurality of projections from a medical-grade polymer with an aspect ratio (longer dimension for an average projections of the plurality of projections divided by a shorter dimension for the average projection of the plurality of projections) in the range of 1/10 to 10. The projections are formed with an interior portion and a plurality of pores that fluidly couple the interior portion and an exterior portion of the projection. The method further includes coupling the plurality of projections to the second side of the dressing body.

According to another illustrative, non-limiting embodiment, an epithelialization dressing for promoting epithelialization of a wound includes a substantially planar member formed from a medical-grade polymer and having a first side and a second, tissue-facing side and formed with a plurality of apertures operable to allow fluid communication between the first side and the second, tissue-facing side. The epithelialization dressing further includes a plurality of pegs coupled to the second, tissue-facing side. The pegs of the plurality of pegs have a longitudinal length in the range of 10 to 5000 microns and have an aspect ratio (longer dimension for an average peg of the plurality of pegs divided by a shorter dimension for the average peg of the plurality of pegs) in the range of 1/10 to 10.

Other features and advantages of the illustrative embodiments will become apparent with reference to the drawings and detailed description that follow.

DETAILED DESCRIPTION

In the following detailed description of the non-limiting, illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The outermost, or most superficial, layer of skin is the epidermis, which itself has numerous layers. The epidermis is adjacent to the dermis. The epidermis may have inwardly directed prolongations of the Malpighian layer that intermesh with the dermal papillae. These prolongations are sometimes called "rete pegs." The rete pegs may provide resistance against shear-induced separation of adjacent layers. In contrast, reepithelialized wounds often do not have as much resistance against shear.

Figure 1:
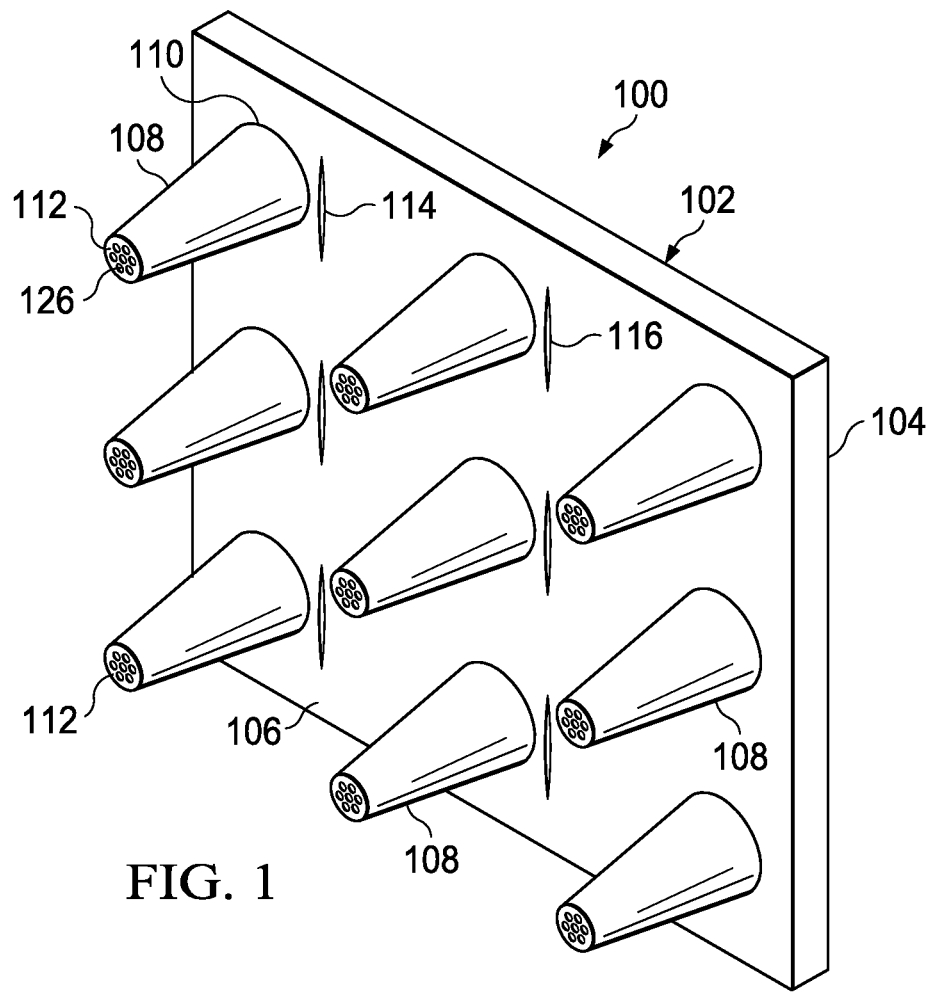
FIG. 1 is a schematic, perspective view of an illustrative, non-limiting embodiment of an epithelialization dressing.
Figure 2:
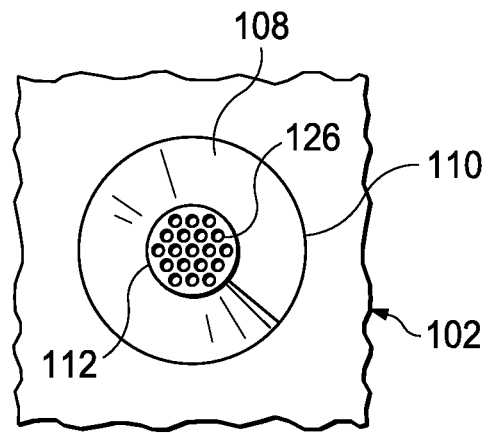
FIG. 2 is a plan view of a portion of the epithelialization dressing of FIG. 1 showing a distal end of a projection.
Figure 3:
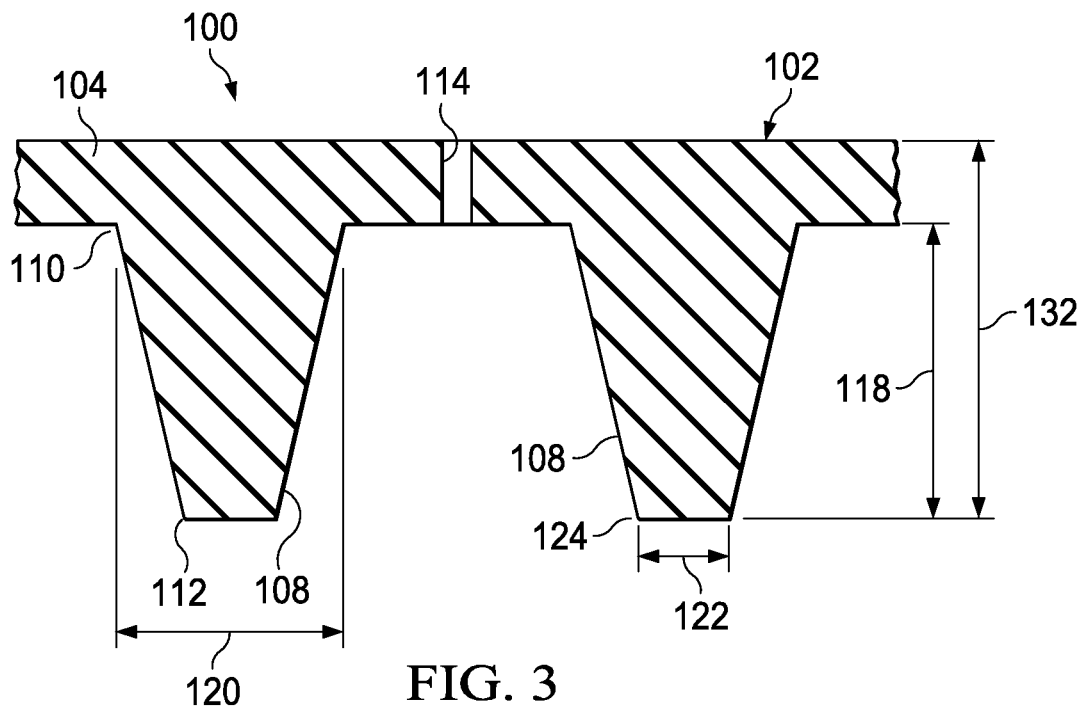
FIG. 3 is a schematic, cross-sectional view of a portion of the epithelialization dressing of FIG. 1.

In the healing process of wounds, the epidermis may regenerate, but the newly formed epithelium often, at least initially, lacks rete pegs. As such, the newly formed epithelium may be easily disrupted or sloughed off. Referring now primarily to FIGS. 1-3, an epithelialization dressing 100 may be used to promote a stronger connection or tethering of layers so as to function effectively as healthy rete pegs. The epithelialization dressing 100 may induce anchor points of epithelium with tissue layers underlying the epidermis by using surface architecture on the epithelialization dressing 100.

Moreover, the epithelialization dressing 100 may hold or secure the epithelium with underlying tissues and thereby protect the epithelium from shear force damage. In addition, the epithelialization dressing 100 may maintain a barrier and obviate the need for repeated repair of the epithelium. The epithelialization dressing 100 may also speed the epithelialization process.

The epithelialization dressing 100 may carry out numerous functions. For example, the epithelialization dressing 100 may function to help manage fluids at a wound to promote epithelialization. As another example, the epithelialization dressing 100 may use physical, chemical, or mechanical properties of the epithelialization dressing 100 to direct development of underlying tissue structures to facilitate strength of the regenerated epidermis. As used herein, unless otherwise indicated, "or" does not require mutual exclusivity.

The epithelialization dressing 100 may be formed with a dressing body 102 having a first side 104 and a second, tissue-facing side 106. The dressing body 102 may take numerous shapes, but is shown as a laminar body, i.e., having an aspect ratio (longer dimension divided by shorter dimension) greater than one in both a longitudinal cross section and lateral cross section. In other words, the dressing body 102 is shown as a flat or substantially flat member. Other shapes may be used for the dressing body 102, such as a rounded member.

The dressing body 102 has a plurality of projections 108 that may be coupled to the second, tissue-facing side 106 of the dressing body 102. Each projection 108 has a proximal end 110 and a distal end 112. The proximal end 110 of each projection 108 is coupled to the second, tissue-facing side 106 of the dressing body 102. A plurality of apertures 114, such as slits 116 or fenestrations, may be formed on a portion of the dressing body 102. The apertures 114 may be slits 116 (longitudinal openings with substantially no material removed) or may be round holes, square holes, or openings of any shape that provide for the transfer of fluids including reduced pressure.

Figure 4:
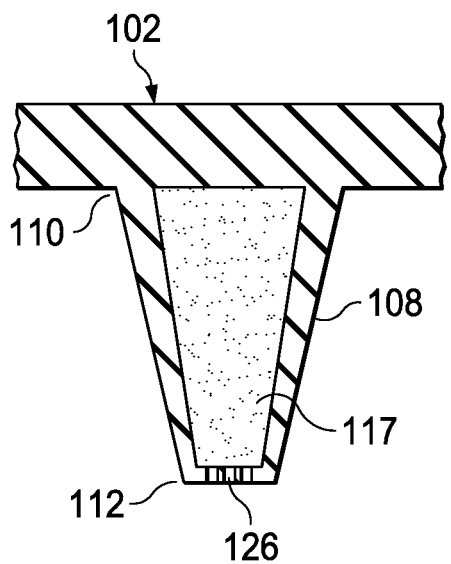
FIG. 4 is a schematic, cross-sectional view of an illustrative projection of an illustrative epithelialization dressing showing a supply reservoir.
Figure 5:
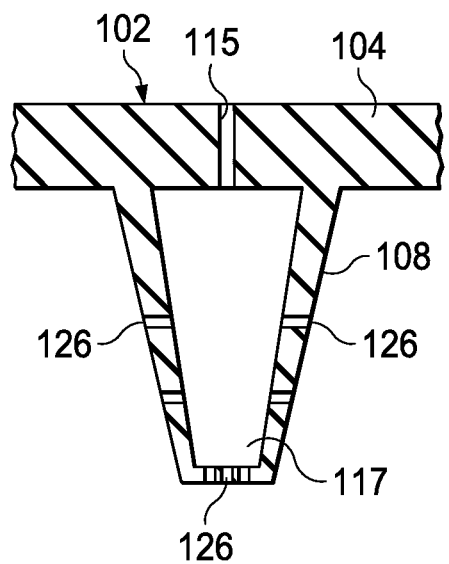
FIG. 5 is a schematic, cross-sectional view of an illustrative projection of an illustrative epithelialization dressing.
Figure 6:
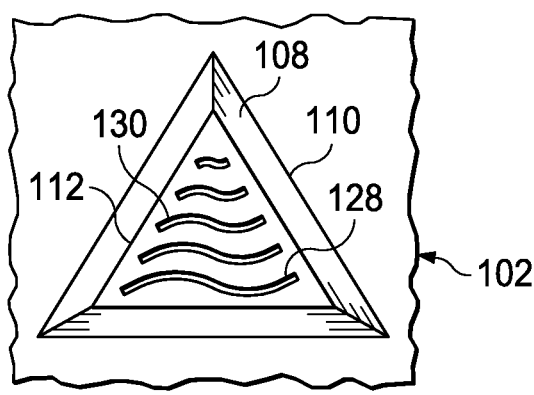
FIG. 6 is a schematic, plan view of an illustrative projection of an illustrative epithelialization dressing.
Figure 7:
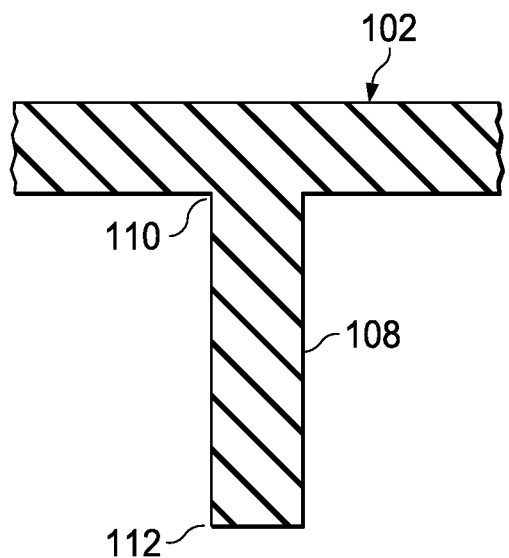
FIG. 7 is a schematic, cross-sectional view of an illustrative projection of an illustrative epithelialization dressing.
Figure 8:
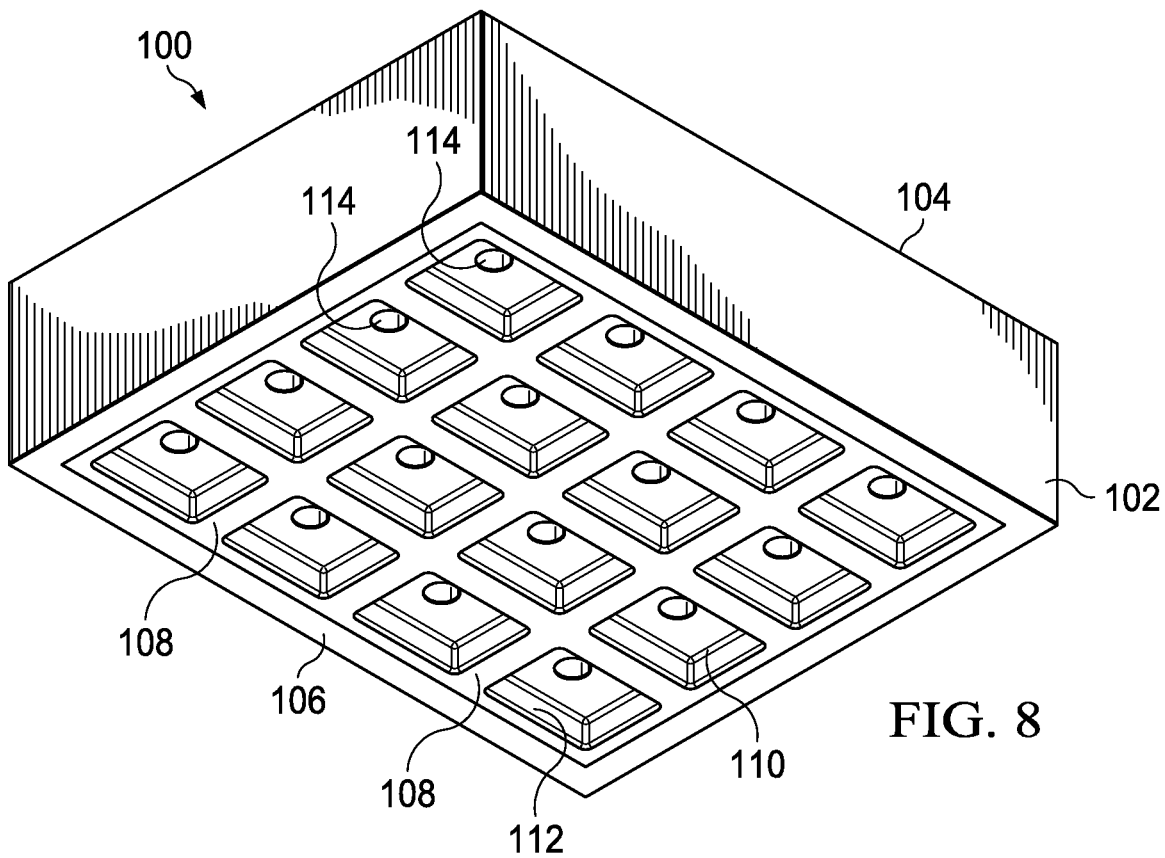
FIG. 8 is a schematic, perspective view of an illustrative epithelialization dressing.
Figure 10:
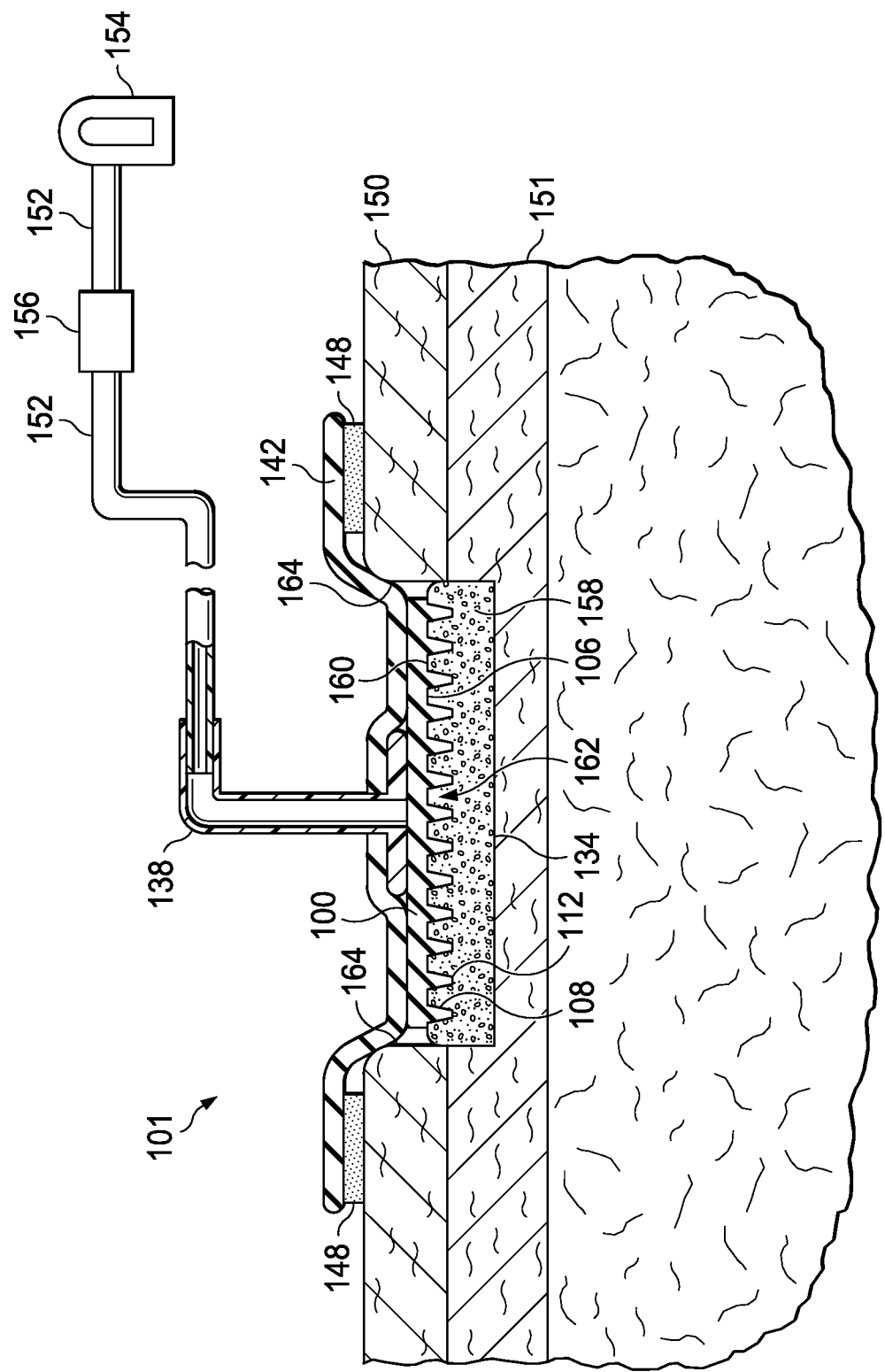
FIG. 10 is a schematic diagram with a portion shown in cross section of an illustrative system for promoting epithelialization.

The projections 108 or other micro-features are for placing on granulation tissue and function to help form epithelium columns 166 (FIG. 11) that may function like rete pegs. The projections 108 may take numerous shapes and sizes. The projections 108 may be for example rods, cones, columns, ridges, grooves, waves, or other features that form cavities 162 (FIG. 10). For example, FIGS. 1-5 present projections 108 as conical members, FIG. 6 presents projections 108 that are triangular in plan view, and FIG. 7 presents a cross section of projections 108 as cylindrical members. FIG. 8 presents a perspective view showing projections 108 that are formed like continuous bars or orthogonal members. The projections 108 may be randomly spaced or spaced with a pattern on the dressing body 102. As shown in FIG. 5, the projections may have a supply reservoir 117 formed within.

Referring now primarily to FIG. 3, each projection 108 may have a longitudinal length 118 (measured from the second, tissue-facing side 106) and a lateral width or diameter 120 at the proximal end 110 and lateral width or diameter 122 at the distal end 112. Each projection 108 may have an aspect ratio (longitudinal length 118/average lateral width) that is in the range of 1/10 to 10 and more typically 1/2 to 2. The average projection of the plurality of projections 108 may have an aspect ratio (longer dimension for an average projections of the plurality of projections divided by a shorter dimension for the average projection of the plurality of projections) in the range of 1/10 to 10 and more typically 1/2 to 2. In other non-limiting examples, the aspect ratio may be 3/10, 5/10, 8/10, 2, 3, 4, 5, 6, 7, 8, or 9. The aspect ratio may be adjusted to help control the level of strain placed on underlying tissue and to help control strain gradients. Controlling the induced strain may help control remodeling of the tissue and may impact stem cell differentiation. An edge 124, or leading edge, on the distal end 112 of the projection 108 may be sharp (orthogonal, 90 degrees, or substantially 90 degrees) or may be rounded to help control strain as well. The projections 108 may all have the same dimensions or properties or may vary one to another.

As shown in FIG. 2, a plurality of pores 126 or small apertures may be formed on the distal end 112 of the projections 108. The pores 126 may also or alternatively be formed at other locations on the projections 108 or dressing body 102. The pores 126 may facilitate removal of fluids near the epithelialization dressing 100, deliver reduced pressure, allow for fluid delivery, or provide for intentional ingrowth of tissue. Pores (not shown) may also be formed on the second, tissue-facing side 106 of the dressing body 102 between the projections 108. With reference to FIG. 4, the pores 126 may help deliver a fluid or other substance, e.g., growth factors, from the supply reservoir 117 to an area near the projection 108.

Referring primarily to FIG. 5, the pores 126 are shown facilitating the delivery of reduced pressure and the removal of fluids near the projections 108. Apertures 115 through the dressing body 102 allow reduced pressure to be delivered from the first side 104 of the dressing body 102 to the supply reservoir 117. The pores 126, which in this embodiment are on the distal end and on a side portion of the projection 108, communicate the reduced pressure from the supply reservoir 117 to an exterior of the projections 108. In this embodiment, the first side 104 of the dressing body 102 is in fluid communication with an exterior of the projections 108. In another embodiment, the projections 108 may be formed with a bicameral reservoir (not shown) having one portion for supplying a substance and another portion for providing reduced pressure.

As shown in FIG. 6, in some embodiments, micro-scale or nano-scale features 128, or sub-features, may be added to the projections 108 typically on the distal end 112. The sub-features 128 may be, for example, grooves 130, ridges, or waves. The sub-features 128 are typically separate from the pores 126, but in other embodiments, could include openings as the pores on the sub-features 128. The micro-scale or nano-scale features 128 may be able to pattern proteins that absorb to the sub-features 128 or promote cell height and direct orientation and migration. If the sub-features 128 are grooves, e.g., the grooves 130, fibroblasts may attach and become oriented according to the features and secrete their matrix proteins in a similar pattern. This may further allow control of tissue development.

The size and shape of the projections 108, the size and spacing of the pores 126, or the sub-features 128 may be used to control the tissue development in order to promote maturation and to enhance the strength of a healing wound against shear stress. The projections 108 or other micro-features may guide tissue growth and remodeling, including cellular orientation and organization. Geometry of the projections 108 or micro-features may be modulated to induce specific load and strain distribution and gradients in the tissue. These modulations may involve aspect ratio, size, spacing, contact area (%), curvature at contact, alternating feature shapes and sizes, biomimetic patterns, and the overlay of micro and sub-features 128. The size and aspect ratio of the projections 108 may be modulated as desired to control stress and strain at the tissue interface.

Numerous materials may be used to form the epithelialization dressing 100, such as a medical-grade polymer, e.g., a silicone or polyurethane, or a biological polymer, e.g., collagen. Other materials from which the epithelialization dressing 100 may be formed include bioresorbable (or resorbable) material, biologic material, or non-resorbable material. As used herein, "bioresorbable" includes a material that enzymatically or chemically degrades into a simple chemical species in vivo, and which may be removed from the body by excretion or metabolism. The material may be an occlusive material. The epithelialization dressing 100 may be non-adherent to tissue growth. The epithelialization dressing 100 may be formed from a non-absorbable material for the dressing body 102. The projections 108 may be formed from a bioresorbable material. In another embodiment, the entire epithelialization dressing 100 is formed from bioresorbable material. The second, tissue-facing surface 106 of the epithelialization dressing 100 may be a moist surface that—other than the projections 108—is relatively smooth as compared to a foam surface. With reference to FIG. 3, the dressing 100 may have a depth 132 that is in the range of 10 to 5000 microns, and more typically between 400 and 600 microns. For example, without limitation, the depth 132 may be 400, 425, 450, 475, 500, 525, 550, 575, 600 microns or another depth.

Referring now to FIG. 8, another illustrative, non-limiting embodiment of an epithelialization dressing 100 is presented. The epithelialization dressing 100 of FIG. 8 may be formed with a dressing body 102 having a first side 104 and a second, tissue-facing side 106. A plurality of projections 108 may be coupled to the second, tissue-facing side 106 of the dressing body 102. Each projection 108 has a proximal end 110 and a distal end 112. The proximal end 110 of each projection 108 is coupled to the second, tissue-facing side 106 of the dressing body 102. The projections 108 form a grid that is used to impinge upon granulation tissue. A plurality of apertures 114 are formed on a portion of the dressing body 102 and are shown as circular openings.

Figure 9:
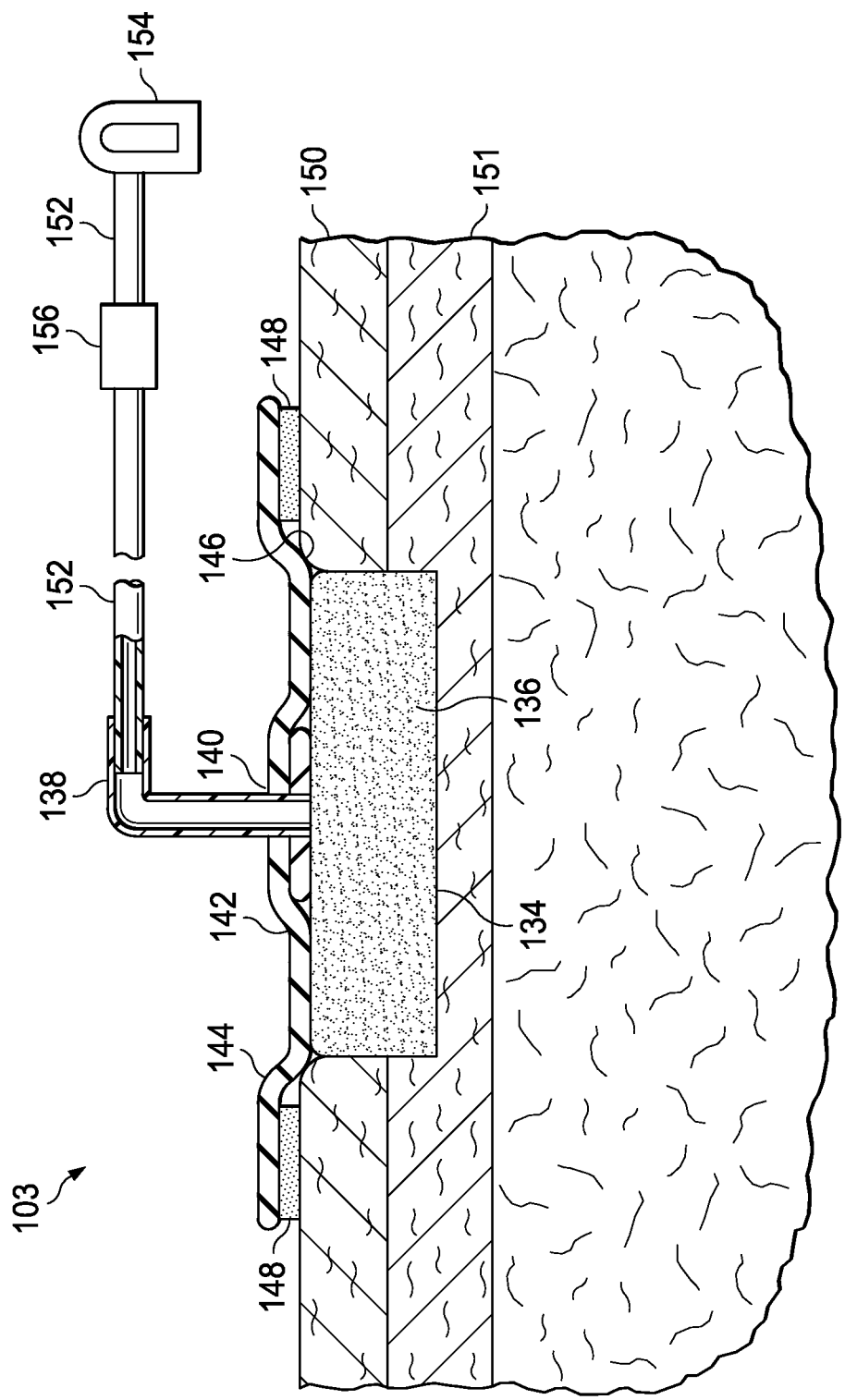
FIG. 9 is a schematic diagram with a portion shown in cross section of an illustrative system for promoting granulation.
Figure 11:
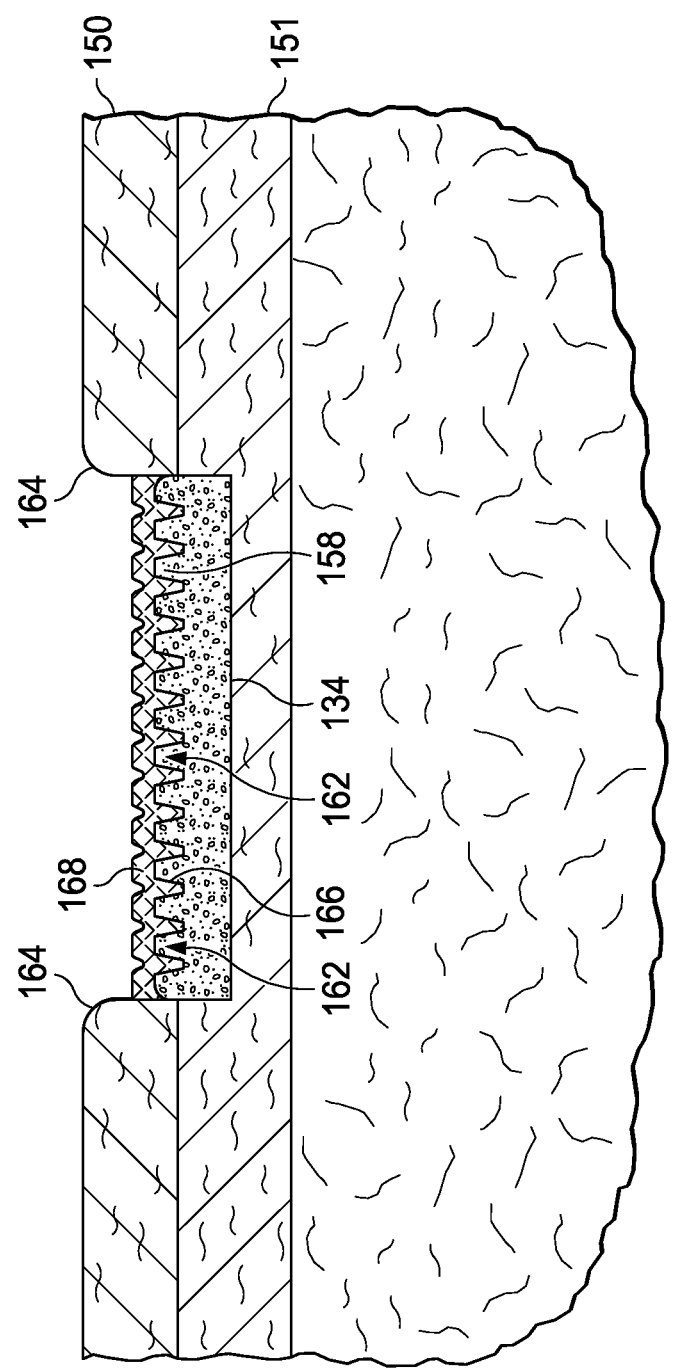
FIG. 11 is a schematic, cross-sectional view of a wound that has been treated to promote epithelialization with an epithelialization dressing according to one illustrative embodiment.

Referring now primarily to FIGS. 9-11, one illustrative, non-limiting process for treating a wound 134 or other tissue site is presented. Referring initially to FIG. 9, the wound 134 is treated with a system 103 to promote granulation. A manifold 136 is disposed proximate the wound 134. The term "manifold" as used herein generally refers to a substance or structure that is provided to assist in applying reduced pressure to, delivering fluids to, or removing fluids from a tissue site or wound 134.

The manifold 136 typically includes a plurality of flow channels or pathways that distribute fluids provided to and removed from the tissue site or wound 134 around the manifold 136. In one illustrative embodiment, the flow channels or pathways are interconnected to improve distribution of fluids provided or removed from the wound 134. The manifold 136 may be a biocompatible material that is capable of being placed in contact with wound 134 and distributing reduced pressure to the wound 134.

Examples of manifolds 136 may include, for example, without limitation, devices that have structural elements arranged to form flow channels, such as, for example, cellular foam, open-cell foam, porous tissue collections, liquids, gels, and foams that include, or cure to include, flow channels. The manifold 136 may be porous and may be made from foam, gauze, felted mat, or any other material suited to a particular biological application. In one embodiment, the manifold 136 is porous foam and includes a plurality of interconnected cells or pores that act as flow channels. The porous foam may be a polyurethane, open-cell, reticulated foam, such as V.A.C.® GranuFoam® material manufactured by Kinetic Concepts, Incorporated of San Antonio, Tex. Other embodiments may include "closed cells." In some situations, the manifold 136 may also be used to distribute fluids such as medications, antibacterials, growth factors, and various solutions to the wound 134. Other layers may be included in or on the manifold 136, such as absorptive materials, wicking materials, hydrophobic materials, and hydrophilic materials.

A reduced-pressure interface 138, e.g., a connector, is disposed proximate the manifold 136 and extends through an aperture 140 in a sealing member 142. The sealing member 142 forms a fluid seal over the wound 134. "Fluid seal," or "seal," means a seal adequate to maintain reduced pressure at a desired site given a particular reduced-pressure source or subsystem involved.

The sealing member 142 may be any material that provides a fluid seal. The sealing member may, for example, be an impermeable or semi-permeable, elastomeric material. "Elastomeric" means having the properties of an elastomer. Elastomeric material generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of sealing member materials include a silicone drape, a 3M Tegaderm® drape, or a polyurethane (PU) drape such as one available from Avery Dennison Corporation of Pasadena, Calif. The sealing member 142 has a first side 144 and a second, tissue-facing side 146.

An attachment device 148 may be used to hold the sealing member 142 against the patient's epidermis 150 or another layer, such as a gasket or additional sealing member. The attachment device 148 may take numerous forms. For example, the attachment device 148 may be a medically acceptable, pressure-sensitive adhesive that extends about a periphery of the sealing member 142. As additional examples, the attachment device 148 may be a double-sided drape tape, paste, hydrocolloid, hydro gel or other sealing devices or elements.

A reduced-pressure delivery conduit 152 may fluidly couple the reduced-pressure interface 138 to a reduced-pressure source 154 that provides reduced pressure. The reduced-pressure source 154 may be any device for supplying a reduced pressure, such as a vacuum pump, wall suction, micro-pump, or other source. While the amount and nature of reduced pressure applied to a tissue site or wound 134 will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, unless otherwise indicated, an increase in reduced pressure or vacuum pressure typically refers to a relative reduction in absolute pressure.

One or more devices, such as device 156, may be included on the reduced-pressure conduit 152. For example, the device 156 may be a fluid reservoir, or collection member, to hold exudates and other fluids removed. Other examples of devices 156 that may be included on the reduced-pressure delivery conduit 152 or otherwise fluidly coupled to the reduced-pressure delivery conduit 152 include the following non-limiting examples: a pressure-feedback device, a volume detection system, a blood detection system, an infection detection system, a flow monitoring system, or a temperature monitoring system. Some of these devices may be formed integrally with the reduced-pressure source 154.

The reduced pressure delivered to the wound 134 helps to fill in the wound defect with new tissue. The reduced pressure may promote fibroblasts to synthesize and develop extracellular matrix components. Granulation tissue fibroblasts produce a matrix for collagen deposition. After sufficient time, granulation tissue 158 (FIG. 10) is deposited on a bed of the wound 134. After the granulation tissue 158 has adequately developed, the sealing member 142 may be removed and the manifold 136 removed. In the example of FIGS. 9 and 10, the granulation tissue 158 has grown outward from near or at a dermis layer 151 to above a lower portion of the epidermis 150.

Referring now primarily to FIG. 10, a system 101 for promoting epithelialization is presented. The epithelialization dressing 100 may placed proximate the granulation tissue 158 with the second, tissue-facing side 106 and projections 108 substantially against the granulation tissue 158. A sealing member 142 is then deployed to provide a fluid seal over the epithelialization dressing 100. In one embodiment (not explicitly shown), the manifold 136 (see FIG. 9) may be placed between the epithelialization dressing 100 (see FIG. 10) and sealing member 142 to facilitate reduced pressure distribution and fluid removal from wound areas distal from reduced-pressure interface 138.

Referring again to the embodiment of FIG. 10, after the reduced-pressure interface 138 and the sealing member 142 (this includes new interfaces and sealing members) are deployed, the reduced-pressure source 154 is again activated. The reduced pressure supplied to the epithelialization dressing 100 may achieve a number of results.

The reduced pressure delivered to the epithelialization dressing 100 may help remove excess fluids from a surface 160 of the wound 134, which has been partially regenerated. Some fluids may remain to assist with signaling and to otherwise promote re-epithelialization. The reduced pressure may provide a compression force on the dressing 100 to help to maintain and control contact between the dressing 100 and the granulation tissue 158 or other tissue. The reduced pressure may be used to cause or control the magnitude of force causing the projections 108 to impinge on the granulation tissue 158 or other tissue. In some embodiments, the pressure may be varied (patterned or random) to provided a variable force delivered by the epithelialization dressing 100 and may thereby further enhance epithelialization.

Referring now primarily to FIGS. 10 and 11, fibroblasts may interact with the second, tissue-facing side 106 of the dressing 100 and form patterned extracellular matrix. Activated keratinocytes migrate from the wound edges 164 around and between the projections 108 and down into the cavities 162 formed by the projections 108 and form an epithelium 168 or new epithelium tissue (FIG. 11). The portion of the matrix going into the cavities 162 will gradually form epithelium columns 166, which may take any shape corresponding substantially to the shape of the projections 108. The epithelium 168 has an x-y pattern around the projections 108 and a pattern in the z-direction as the epithelium 168 moves into the cavities 162 to form the epithelium columns 166. The cavities 162 formed by the projections 108 will extend into the adjacent layer of granulation tissue 158 and help form the epithelium columns 166. The epithelium columns 166 act functionally like rete pegs between the epidermis 150 and dermis 151 and thereby may provide anchor points resistant against external forces to keep the involved tissue layers adherent. The epithelium columns 166 form simulated rete pegs.

Referring now primarily to FIG. 11, the wound 134 is shown after dressing 100 has been removed. (The surface of the epithelium 168 may be more or less flush with the intact epidermis 150 than shown). The dressing 100 may stay in place on the wound for a set time of any duration and typically between one to six days. In this illustrative, non-limiting embodiment, the epithelium 168 covers the granulation tissue 158. The epithelium columns 166 fill the cavities 162 and extend into the granulation tissue 158. In some embodiments (not explicitly shown), the epithelium columns 166 extend into a portion of the dermis 151. The epithelium columns 166 provide additional shear resistance for the epithelium 168.

It should be noted that while the process of FIGS. 9-11 shows the use of reduced-pressure treatment to promote formation of the granulation tissue 158, the dressing 100 may be used independently of such a step. In addition, while the process and system 100 has been described as using reduced pressure, it should be understood that the dressing 100 may be used without reduced pressure. In this illustrative process, the dressing 100 may further include a hydrophilic material, e.g., hydrophilic foam or capillaries, on the first side 104 to help remove fluids through the apertures 114 and a bolster, tape, compression wrap, or other device may be used to provide a compression force on the dressing 100 to assure contact between the dressing 100 and the tissue.

Numerous alternatives or additions may be involved with the illustrative, non-limiting dressing 100, system 101, or the process. Some have already been mentioned and other, non-exhaustive examples are now mentioned. In another illustrative process, the dressing 100 may be made from a reabsorbable material that degrades. The projections 108 may include supply reservoirs 117 that hold encapsulated stem cells, keratinocytes, growth factors, soluble factors, or other substance. As the degradation reaches a certain level, the substance within the supply reservoirs 117 is delivered to the cavities 162 and tissue. The substance then fills or helps fill the cavity 162 and helps promote further healing.

In another illustrative, non-limiting embodiment, the dressing 100, system 101, or the processes may be used with other tissues. For example, in addition to epithelial tissue, endothelial and mucosal linings may benefit. Other embodiments may also be used for treating tendons, ligaments, muscles, or cartilage to add inherent resistance to the forces that actively work to separate these tissues.

In another illustrative, non-limiting example, the dressing 100 may be used as an aspect of promoting granulation and epithelialization. The dressing 100 may include the projections 108 with pores 126 on the distal end 112 and also all along the side walls of the projections 108. Ingrowth of granulation tissue 158 into the pores 126 is promoted. If reduced pressure is utilized, the reduced pressure may help pull tissue into the pores 126. Once the granulation tissue 158 has grown into and around the projections 108, the advancing keratinocytes may follow the granulation tissue 158 and overlay the granulation tissue 158. In addition or as a separate alternative, the dressing 100 may be bioresorbable and degrade over time. The degradation should not negatively impact keratinocyte proliferation. In addition, the projections 108 may have supply reservoirs 117 with active soluble factors that enhance local keratinocyte differentiation. The thickening of the keratinocytes in this area may fill the cavity 162 formed by the projections 108.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. An epithelialization dressing for forming anchor points between neo-epithelium tissue and an adjacent layer of tissue, the epithelialization dressing comprising:
   a dressing body having a first side and a second side positioned opposite the first side, the second side configured to face tissue;
   a plurality of projections, each projection having a proximal end, a distal end, an interior portion, and an exterior portion, and further comprising a supply reservoir formed in the interior portion, each distal end including at least one pore in fluid communication between the supply reservoir and the exterior portion, each proximal end coupled to the second side of the dressing body; and
   a plurality of apertures, each of the apertures being individually disposed through the first side and the second side of the dressing body, wherein the plurality of projections are positioned between the plurality of apertures on the second side.

2. The epithelialization dressing of claim 1, further comprising sub-features formed on the distal end of at least one of the plurality of projections, wherein the sub-features are selected from the group consisting of: grooves, ridges, and waves.

3. The epithelialization dressing of claim 1, wherein the plurality of projections further comprise supply reservoirs formed in the interior portion of the projections and wherein the reservoirs contain soluble factors.

4. The epithelialization dressing of claim 1, wherein the plurality of projections further comprise supply reservoirs formed in the interior portion of the projections and wherein the plurality of projections and the dressing body are formed of a bioresorbable material.

5. The epithelialization dressing of claim 1, wherein the projections of the plurality of projections have an aspect ratio (longer dimension for an average projection of the plurality of projections divided by a shorter dimension for the average projection of the plurality of projections) in the range of 1/10 to 10.

* * * * *